United States Patent
Kawano et al.

(10) Patent No.: US 10,302,562 B2
(45) Date of Patent: May 28, 2019

(54) GLOSS EVALUATION METHOD AND GLOSS EVALUATION DEVICE

(71) Applicant: KONICA MINOLTA, INC., Chiyoda-ku (JP)

(72) Inventors: Toshio Kawano, Sakai (JP); Yushi Nobumoto, Takatsuki (JP)

(73) Assignee: KONICA MINOLTA, INC., Tokyo (JP)

( * ) Notice: Subject to any disclaimer, the term of this patent is extended or adjusted under 35 U.S.C. 154(b) by 389 days.

(21) Appl. No.: 15/033,733

(22) PCT Filed: Sep. 16, 2014

(86) PCT No.: PCT/JP2014/074397
§ 371 (c)(1),
(2) Date: May 2, 2016

(87) PCT Pub. No.: WO2015/072223
PCT Pub. Date: May 21, 2015

(65) Prior Publication Data
US 2016/0258865 A1 Sep. 8, 2016

(30) Foreign Application Priority Data

Nov. 14, 2013 (JP) .................................. 2013-235967

(51) Int. Cl.
*G01N 21/57* (2006.01)
*G01N 21/55* (2014.01)
(Continued)

(52) U.S. Cl.
CPC ................ *G01N 21/57* (2013.01); *G01J 3/50* (2013.01); *G01N 21/27* (2013.01); *G01N 21/55* (2013.01); *G01N 2021/556* (2013.01)

(58) Field of Classification Search
CPC ........ G01N 21/57; G01N 21/27; G01N 21/55; G01N 2021/556; G01J 3/50
See application file for complete search history.

(56) References Cited

U.S. PATENT DOCUMENTS

2008/0245979 A1* 10/2008 Banton .................. G01N 21/57
250/559.4

FOREIGN PATENT DOCUMENTS

| JP | 6-003135 | 1/1994 |
| JP | 10-073487 | 3/1998 |

(Continued)

OTHER PUBLICATIONS

Shafer S A, "Using Color to Separate Reflection Components," Color Research and Application, vol. 10, No. 4, pp. 210-218, 1985.
(Continued)

*Primary Examiner* — Hina F Ayub
*Assistant Examiner* — Amanda Merlino
(74) *Attorney, Agent, or Firm* — Cozen O'Connor (57) ABSTRACT

In a gloss evaluation method and a gloss evaluation apparatus according to the present invention, an intensity P of specular light obtained by illuminating an object to be measured with illumination light of spectral irradiance emitted from the reference machine is obtained from an intensity of specular light obtained by illuminating the object to be measured with first illumination light of spectral irradiance from a relevant machine, based on an intensity b of dispersed reflected light obtained by illuminating the object to be measured with the first illumination light, and a spectral reflectance of diffuse reflection light obtained by illuminating the object to be measured with predetermined second illumination light from a different illuminating angle.

17 Claims, 8 Drawing Sheets

(51) Int. Cl.
*G01J 3/50* (2006.01)
*G01N 21/27* (2006.01)

(56) References Cited

FOREIGN PATENT DOCUMENTS

| | | |
|---|---|---|
| JP | 2004-317131 | 11/2004 |
| JP | 2010-243353 | 10/2010 |

OTHER PUBLICATIONS

T. Tanaka, "Shin Coating Zairyo no Bussei to Hyoda Coating Maku no Hymen Tokusei to Shikenho (2)", Toso Gijustu, vol. 41, No. 13, pp. 103-106, Jan. 12, 2002.

\* cited by examiner

GLOSS EVALUATION METHOD AND GLOSS EVALUATION DEVICE

RELATED APPLICATIONS

This is a U.S. National Phase Application under 35 USC 371 of International Application PCT/JP2014/074397 filed on Sep. 16, 2014.

This application claims the priority of Japanese application no. 2013-235967 filed Nov. 14, 2013, the entire content of which is hereby incorporated by reference.

TECHNICAL FIELD

The present invention relates to a technique for evaluating a gloss of an object.

BACKGROUND ART

As a method of measuring a gloss of an object surface, a specular glossiness measurement method (JIS-Z8741) has been widely known in which an amount of light reflected is measured in a specular direction with light emitted to the surface to obtain a gloss level. Such a specular glossiness measurement method represents an index indicating only an intensity of a beam reflected in the specular direction, a specular glossiness measured by the specular glossiness measurement method and visual glossiness subjectively evaluated by human are not always conforms with each other.

Thus, another method is proposed which measures light reflected from a plurality of angles to obtain an evaluation value closer to the subjective human evaluation value. For example, there is a method for obtaining an evaluation value about gloss of an object with reference to a gloss index value obtained based on specular light from an object and index values about luminance and saturation based on diffuse reflection light (see Patent Literature 1). Moreover, there is a method for obtaining an evaluation value of glossiness of an object, with reference to a gloss variation evaluation value obtained based on a luminance component of specular light, a gloss reference value obtained based on luminance components of specular light and diffuse reflection light, and a chromaticity variation index value about an amount of variation in color of specular light and diffuse reflection light (see Patent Literature 2).

Usually, a gloss evaluation apparatus for evaluating a gloss of an object is formed to output an identical evaluation value (measurement value) for identical object, for shipment.

However, the gloss evaluation apparatus used for a long time may output different evaluation values for the identical object. This case may be caused by for example temporal change of a light source for emitting light for gloss measurement, or a light receiving element for receiving reflected light. Further, a light source or a light receiving element may have an individual difference in intrinsic characteristic. Still further, a use environment thereof, for example, an ambient temperature may cause variation in evaluation value.

CITATION LIST

Patent Literature

Patent Literature 1: JP 2004-317131 A
Patent Literature 2: JP 2010-243353 A

SUMMARY OF INVENTION

The present invention has been made in view of the above problems, and an object of the present invention is to provide a gloss evaluation method and a gloss evaluation apparatus which reduce a difference (variation) between a gloss evaluation value obtained by measuring an object using a gloss evaluation apparatus, and a gloss evaluation value obtained by measuring the object using a reference gloss evaluation apparatus (master machine (reference machine)).

In the gloss evaluation method and the gloss evaluation apparatus according to an embodiment of the present invention, an intensity P of specular light obtained by illuminating an object to be measured with illumination light of spectral irradiance $L(\lambda)$ emitted from a reference machine is obtained from an intensity a of specular light, based on an intensity b of dispersed reflected light, and a spectral reflectance $R(\lambda)$ of diffuse reflection light. The intensity a of specular light is obtained by illuminating the object to be measured with first illumination light of spectral irradiance $L'(\lambda)$ from a relevant machine, the intensity b of dispersed reflected light is obtained by illuminating the object to be measured with the first illumination light, and the spectral reflectance $R(\lambda)$ of diffuse reflection light is obtained by illuminating the object to be measured with predetermined second illumination light from a different illuminating angle. Thus, the gloss evaluation method and the gloss evaluation apparatus can obtain, as a gloss evaluation value obtained by measuring the object to be measured, a gloss evaluation value in which a difference (variation) from the gloss evaluation value measured by the reference gloss evaluation apparatus (master machine (reference machine)) is reduced.

The above description, another object, features, and advantages of the present invention will be apparent from the following detailed description and appended drawings.

DESCRIPTION OF EMBODIMENTS

One embodiment according to the present invention will be described below based on the drawings. Note that, in the drawings, the same configurations are denoted by the same reference signs, and description thereof is appropriately omitted. In the present specification, configurations are collectively denoted by a reference sign without a subscript, and individual configurations are denoted by reference signs with subscripts.

A gloss evaluation apparatus 100 according to an embodiment calculates a gloss evaluation value obtained by measurement using a master machine defined as a reference machine to reduce variation in evaluation value (measurement value) caused by a difference between machines in a gloss evaluation apparatus being so-called mass-produced machine, or a difference in measurement conditions (ambient temperature environments, temporal change of a light source).

<Configuration>

Figure 1:
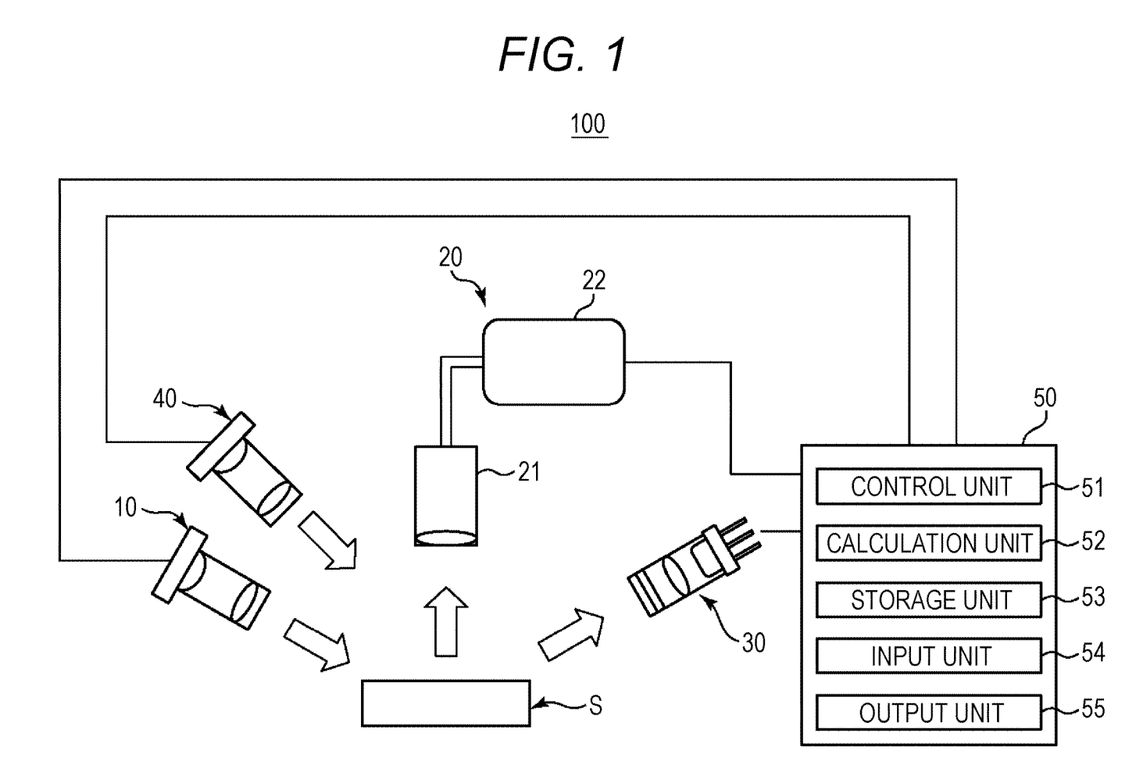
FIG. 1 is a schematic diagram illustrating an example of a whole gloss evaluation apparatus according to an embodiment.
Figure 2:
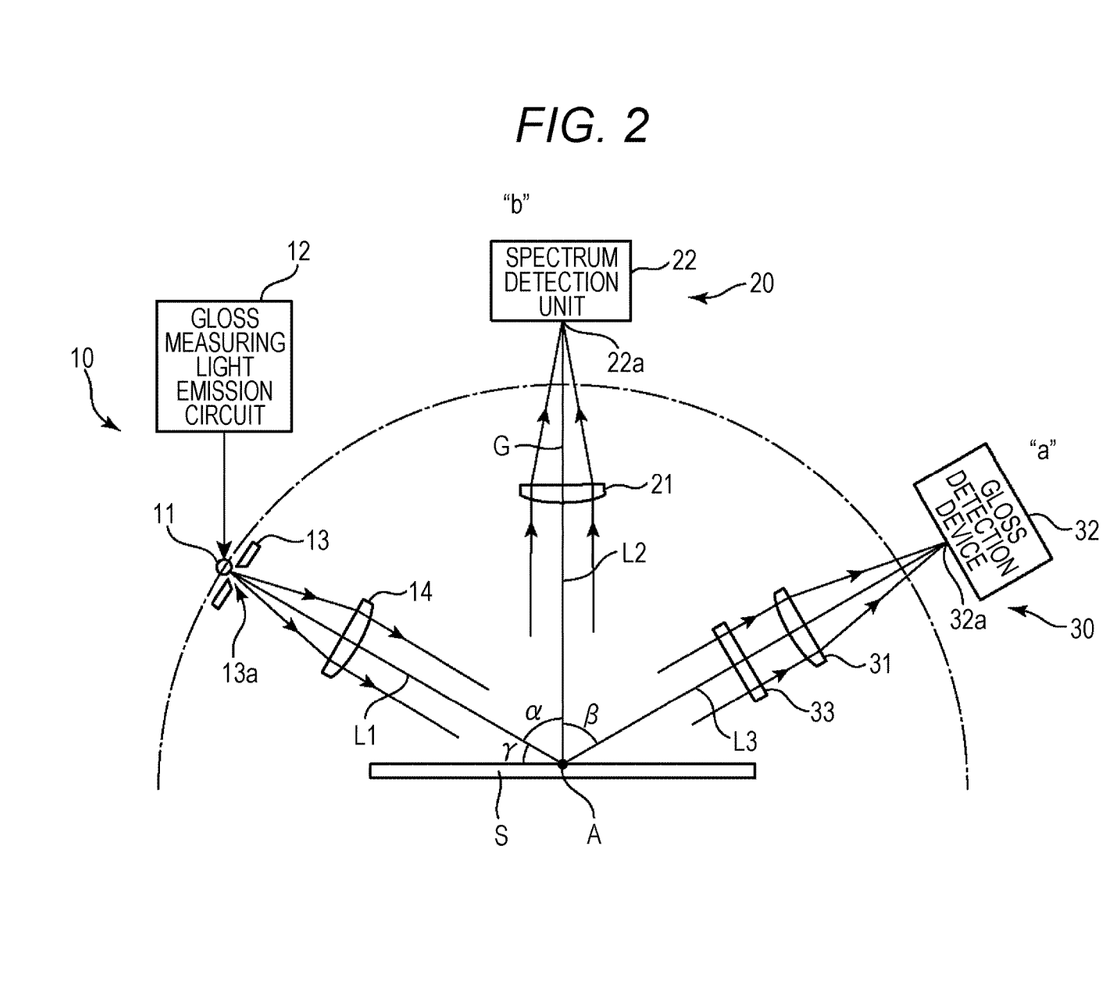
FIG. 2 is a diagram illustrating the gloss evaluation apparatus of FIG. 1 in which a first illumination unit emits light.
Figure 3:
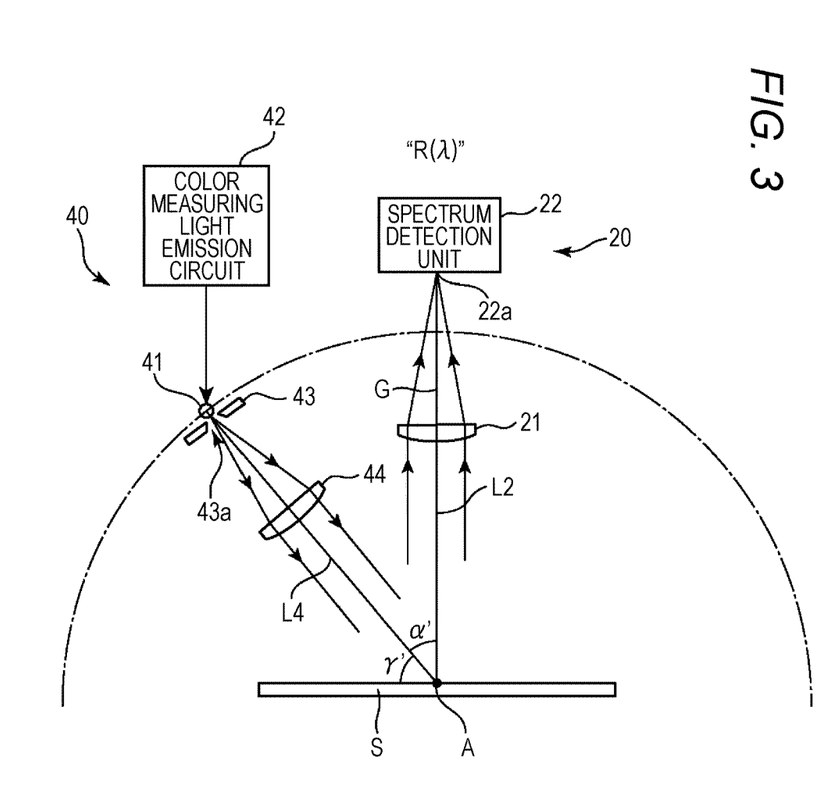
FIG. 3 is a diagram illustrating the gloss evaluation apparatus of FIG. 1 in which a second illumination unit emits light.
Figure 4:
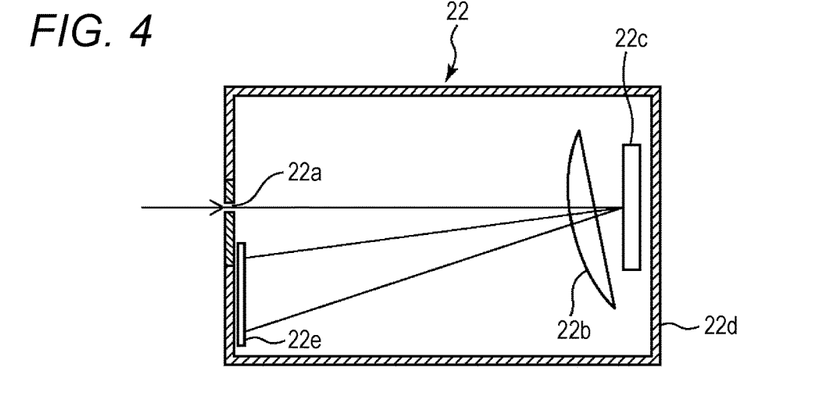
FIG. 4 is a configuration diagram illustrating an example of a spectrum detection unit in the gloss evaluation apparatus of FIG. 1.

FIG. 1 is a diagram illustrating an example of a whole configuration of the gloss evaluation apparatus 100. Note that the master machine includes a configuration similar to that of the gloss evaluation apparatus 100. FIG. 2 is a diagram illustrating a first illumination unit 10 of the gloss evaluation apparatus 100, in which the first illumination unit 10 emits light, and FIG. 3 is a diagram illustrating a second illumination unit 40 emitting light. FIG. 4 is a configuration diagram illustrating an example of a spectrum detection unit 22.

Figure 5:
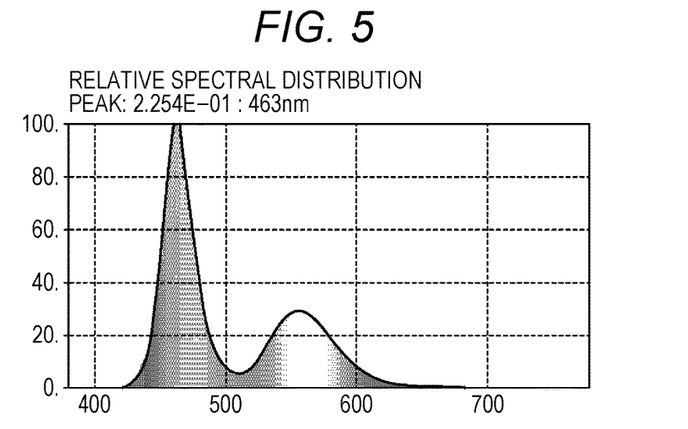
FIG. 5 is a graph illustrating an example of a spectral irradiance $L(\lambda)$ of illumination light from a first illumination unit in the gloss evaluation apparatus of FIG. 1.
Figure 6:
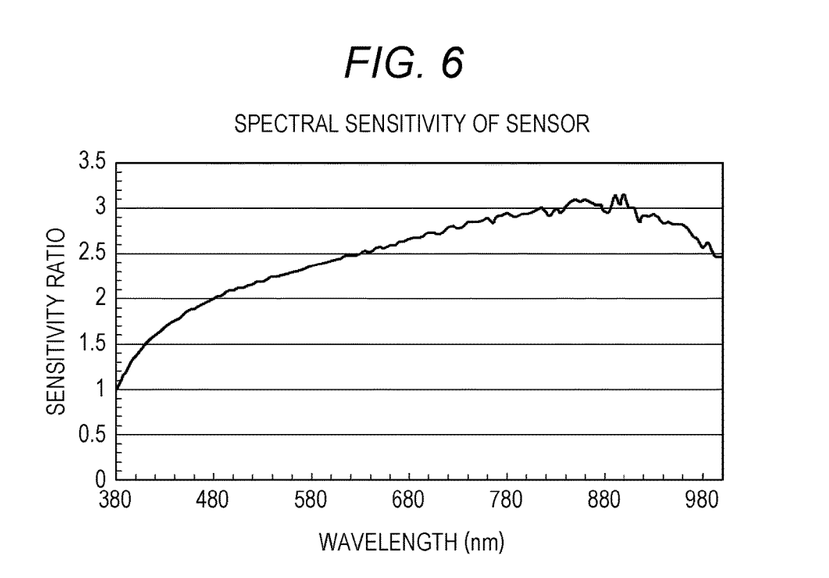
FIG. 6 is a graph illustrating an example of a spectral sensitivity $S(\lambda)$ of a gloss detection device in the gloss evaluation apparatus of FIG. 1.
Figure 7:
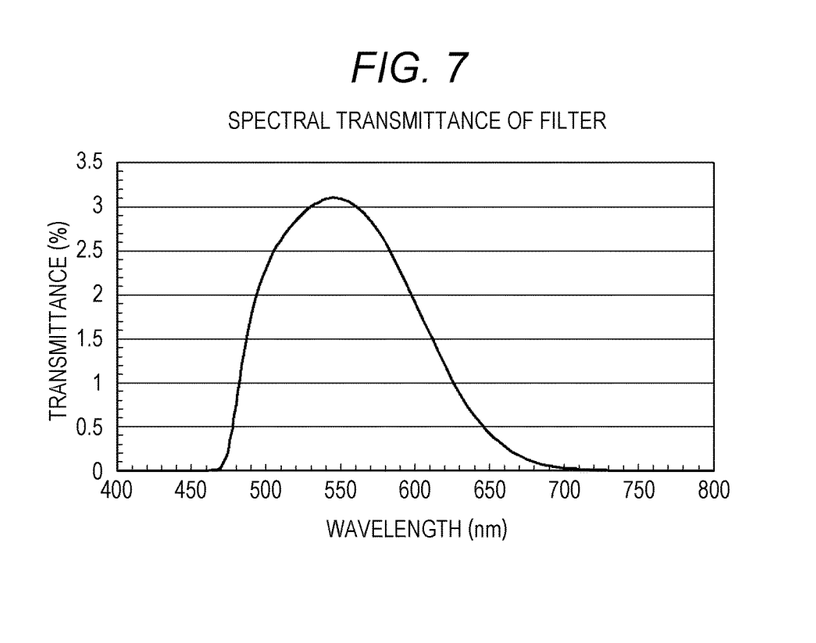
FIG. 7 is a graph illustrating an example of a spectral transmittance $F(\lambda)$ of a filter in the gloss evaluation apparatus of FIG. 1.
Figure 8:
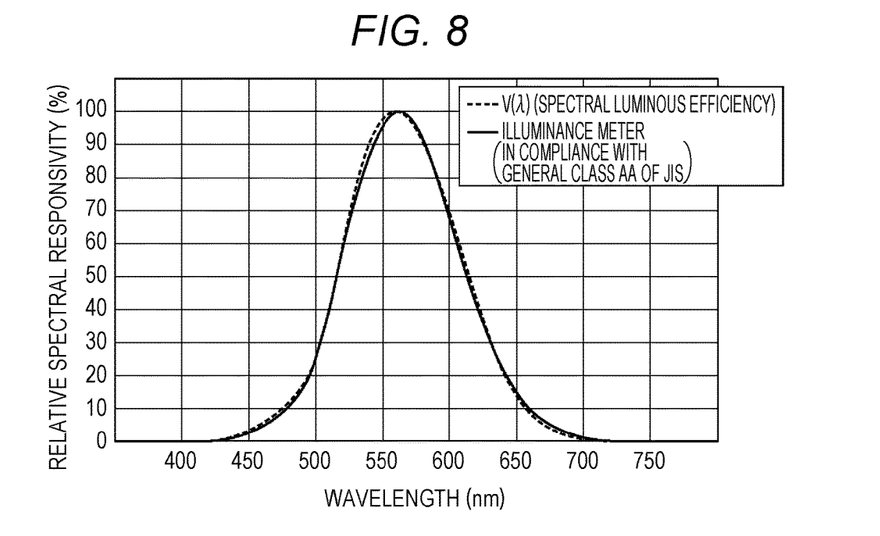
FIG. 8 is a graph illustrating an example of a spectral luminous efficiency $V(\lambda)$.
Figure 9:
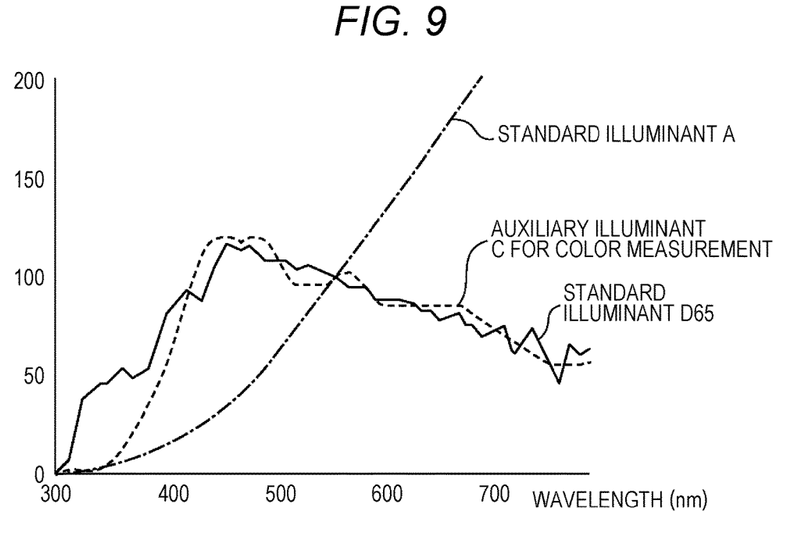
FIG. 9 is a graph illustrating an example of spectral distributions $Sc(\lambda)$ of standard illuminants.

FIG. 5 is a graph illustrating an example of a spectral irradiance $L(\lambda)$ of illumination light. In FIG. 5, a horizontal axis represents wavelength, and a vertical axis represents irradiance. FIG. 6 is a graph illustrating an example of a spectral sensitivity $S(\lambda)$ of a light receiving element. In FIG. 6, a horizontal axis represents wavelength, and a vertical axis represents sensitivity. FIG. 7 is a graph illustrating an example of a spectral transmittance $F(\lambda)$ of a filter. In FIG. 7, a horizontal axis represents wavelength, and a vertical axis represents transmittance. FIG. 8 is a diagram illustrating an example of a spectral luminous efficiency $V(\lambda)$. In FIG. 8, a horizontal axis represents wavelength, and a vertical axis represents responsivity. Moreover, FIG. 9 is a diagram illustrating an example of spectral distributions $Sc(\lambda)$ of standard illuminants. In FIG. 9, a horizontal axis represents wavelength, and a vertical axis represents irradiance. In FIG. 9, a broken line represents a spectral distribution of an auxiliary illuminant C for color measurement, a solid line represents a spectral distribution of a standard illuminant D65, and a dashed line represents a spectral distribution of a standard illuminant A.

The gloss evaluation apparatus 100 includes the first illumination unit 10, a diffuse reflection light receiving unit 20, a specular light reception unit 30, the second illumination unit 40, and a calculation control unit 50. The first illumination unit 10, the diffuse reflection light receiving unit 20, the specular light reception unit 30, and the second illumination unit 40 are controlled by the calculation control unit 50, and respectively output measured values to the calculation control unit 50.

As illustrated in FIG. 2, the first illumination unit 10 includes a gloss measuring light source 11, a gloss measuring light emission circuit 12, a beam restriction plate 13, and a collimator lens 14. The gloss measuring light source 11 includes a halogen lamp, a light-emitting diode (LED), or the like, the gloss measuring light emission circuit 12 drives the gloss measuring light source 11, and the beam restriction plate 13 restricts a beam output (radiated) from the gloss measuring light source 11. The gloss measuring light source 11 is a light source emitting predetermined light used for obtaining an evaluation value about gloss, and is fixedly disposed at a position having a predetermined angle (herein 60°) from a normal line (normal line of surface to be measured) G in the surface to be measured of the object S to be measured. The beam restriction plate 13 has an opening 13a disposed to be at a focal position of the collimator lens 14, and a beam (optical axis L1) emitted from the gloss measuring light source 11 passes through the opening 13a of the beam restriction plate 13, is collimated (parallelized) by the collimator lens 14 into a parallel beam, and is directed to the surface to be measured of the object S to be measured. Illumination light from the first illumination unit 10 has a spectral irradiance which is, for example, the spectral irradiance illustrated in FIG. 5. The example of the spectral irradiance illustrated in FIG. 5 has a maximum peak substantially at a wavelength of approximately 463 nm, and has a second maximum peak at a wavelength of approximately 550 nm.

The diffuse reflection light receiving unit 20 includes a light receiving optical system 21 for convergence of a beam (optical axis L2) reflected from the object S to be measured, and the spectrum detection unit 22. The spectrum detection unit 22 is disposed at an imaging position of the light receiving optical system 21, and measures a spectral intensity of light passing through the light receiving optical system 21, and passing through an entrance slit 22a. The optical axis L2 of the diffuse reflection light receiving unit 20 and the surface to be measured of an object S to be measured intersect at right angles at an intersection point A.

Here, FIG. 4 is a configuration diagram illustrating an example of the spectrum detection unit 22. As illustrated in FIG. 4, the spectrum detection unit 22 has a box-shaped housing case 22d having an entrance slit 22a formed at an appropriate position, and includes a lens 22b, a diffraction grating 22c, and a light reception sensor 22e, in the box-shaped housing case 22d. The lens 22b parallelizes light to be measured passing through the entrance slit 22a to direct the light to the diffraction grating 22c, and form a dispersion image of the entrance slit 22a dispersed by the diffraction grating 22c, on a light receiving surface of the light reception sensor 22e. The diffraction grating 22c has a function for reflecting and dispersing incident measurement light to different angles according to the wavelength, and forms the dispersion image of the entrance slit 22a on the light reception sensor 22e. The light reception sensor 22e includes a plurality of light receiving channels (pixels) disposed at predetermined intervals, including for example a silicon photodiode array having silicon photodiodes disposed in line in one direction. Dispersed light (dispersion image of the entrance slit) entering each of the light receiving channels of the light reception sensor 22e is converted to an electric current by photoelectric conversion function of each of the photodiodes, and output to the calculation control unit 50.

The second illumination unit 40 and the diffuse reflection light receiving unit 20 are disposed to have a predetermined geometry, for example, a 45 degree/0 degree geometry.

As illustrated in FIG. 2, the specular light reception unit 30 includes the filter 33 for filtering a beam reflected from the object S to be measured a light receiving optical system 31 for focusing the beam, and a gloss detection device 32. The gloss detection device 32 is disposed at an imaging position of the light receiving optical system 31, and outputs an amount (light intensity) of a beam entering from an entrance slit 32a for limiting light passing through the light receiving optical system 31. The gloss detection device 32 has, for example, the spectral sensitivity S(λ) of FIG. 6. The example of the spectral sensitivity S(λ) illustrated in FIG. 6 is substantially gradually increased as the wavelength is increased, has a peak (maximum value) at a wavelength of approximately 880 nm, and then is gradually reduced.

The filter 33 is preferably a filter (e.g., bandpass filter, cutoff filter) for transmitting a desired wavelength band, and includes for example an optical absorption filter or an optical interference filter. The filter 33 has the spectral transmittance F(λ) set to satisfy the following relational expression. That is, a result of multiplication of the spectral irradiance L(λ), the spectral sensitivity S(λ), and the spectral transmittance F(λ), and a result of multiplication of a spectral distribution Sc(λ) of a standard illuminant and the spectral luminous efficiency V(λ) have a proportional relationship.

$$L(\lambda) \times S(\lambda) \times F(\lambda) \square Sc(\lambda) \times V(\lambda)$$

wherein, L(λ) is a spectral irradiance of the gloss measuring light source 11 of the first illumination unit 10, S(λ) is a spectral sensitivity of the specular light reception unit 30, and F(λ) is a spectral transmittance of the filter 33. Sc(λ) is a spectral distribution of a standard illuminant, and V(λ) is a spectral luminous efficiency (human eye sensitivity) defined by JIS or the like. That is, the spectral transmittance F(λ) of the filter 33 is set so that a responsivity of the specular light reception unit 30 receiving illumination light from the first illumination unit 10 through the filter 33 has the human eye sensitivity, in which the filter 33 has the spectral transmittance F(λ), the illumination light from the first illumination unit 10 has the spectral irradiance L(λ), and the specular light reception unit 30 has the spectral sensitivity S(λ).

The filter 33 has, for example, the spectral transmittance F(λ) of FIG. 7. The example of the spectral transmittance F(λ) illustrated in FIG. 7 has a peak at a wavelength of approximately 540 nm. The example of the spectral luminous efficiency V(λ) is illustrated in FIG. 8. In the graph, a broken line represents the spectral luminous efficiency, and a solid line represents the responsivity of the specular light reception unit 30. The example of the spectral distributions Sc(λ) of the standard illuminants is illustrated in FIG. 9. The second illumination unit 40 has a color measuring light source 41 which emits light having a spectral distribution of the auxiliary illuminant C for color measurement, represented by a broken line. Note that, in FIG. 9, a solid line represents the spectral distribution of the standard illuminant D65 defined by International Commission on Illumination (CIE), and a dashed line represents the spectral distribution of the standard illuminant A defined by CIE.

The specular light reception unit 30 is fixedly disposed at a position in a specular direction (including a position around the specular direction) located at a specular angle relative to an angle α of illumination (illuminating angle γ) of an illumination system. That is, the specular light reception unit 30 is fixedly disposed at a position in a light receiving direction to have an angle β of reflection (angle between a normal line G and a reflected ray, being in a common plane with an angle α of incidence, being equal to the angle of incidence) with respect to the angle α of incidence (angle of an incident ray from the normal line G at an incident point) (α=β). Thus, the first illumination unit 10 and the specular light reception unit 30 are disposed for example to have a 60 degree/60 degree geometry.

Next, as illustrated in FIG. 3, the second illumination unit 40 includes the color measuring light source 41, a color measuring light emission circuit 42, a beam restriction plate 43, and a collimator lens 44, in which the color measuring light source 41 includes a halogen lamp, a light-emitting diode (LED), or the like, the color measuring light emission circuit 42 drives the color measuring light source 41, and a beam restriction plate 43 restricts a beam output from the color measuring light source 41. The color measuring light source 41 is a light source for emitting predetermined light used for obtaining the evaluation value about gloss, and is fixedly disposed at a position having a predetermined angle (here, 45°) from the normal line G of the surface to be measured of the object S to be measured. The beam restriction plate 43 has an opening 43a disposed to be at a focal position of the collimator lens 44, and a beam (optical axis L4) emitted from the color measuring light source 41 passes through the opening 43a of the beam restriction plate 43, is collimated by the collimator lens 44 into a parallel beam, and is directed to the surface to be measured of the object S to be measured.

The calculation control unit 50 is constituted by, for example, a computer including a central processing unit (CPU), a storage unit such as a read only memory (ROM) for storing a program defining operation of the CPU, a random access memory (RAM) for temporarily storing data, or the like, and the calculation control unit 50 includes a control unit 51, a calculation unit 52, a storage unit 53, an input unit 54, and an output unit 55, and controls the operation of the gloss evaluation apparatus 100.

The control unit 51 is configured to control light emission operation (lighting, extinction) of the gloss measuring light source 11 and the color measuring light source 41, and controls the drive of the gloss measuring light emission circuit 12 and the color measuring light emission circuit 42 to control the light emission operation thereof. The control unit 51 controls light reception operation of the diffuse reflection light receiving unit 20 and the specular light reception unit 30

The calculation unit 52 performs calculation processing for obtaining a reflection characteristic value, that is, the evaluation value about gloss (hereinafter, referred to as "gloss evaluation value") of the object S to be measured, based on output signals from the diffuse reflection light receiving unit 20 and the specular light reception unit 30. The calculated gloss evaluation value is displayed on the output unit 55. Note that details of a process of finding the gloss evaluation value performed by the calculation unit 52 will be described later in <process of finding gloss evaluation value>. The control unit 51 and the calculation unit 52 are functionally provided in the CPU in the present embodiment.

The storage unit 53 previously stores the spectral irradiance L(λ) of the first illumination unit 10 of the master machine (reference machine) and the spectral sensitivity S(λ) of the specular light reception unit 30 which are used for calculation of the gloss evaluation value by the calculation unit 52.

The input unit 54 is a device for inputting various data or various commands, for example, for starting evaluation of a gloss, to the gloss evaluation apparatus 100, and the input unit 54 includes for example a keyboard or a mouse.

The output unit 55 is a device for outputting the commands, the data, calculation results of the gloss evaluation apparatus 100, or the like input from the input unit 54, and the output unit 55 includes for example a display device such as a cathode ray tube (CRT) display, or a liquid crystal display (LCD), a printing device such as a printer, or the like.

<Process of Finding Gloss Evaluation Value>

First, the gloss evaluation apparatus 100 obtains, using the following formula (1), an index value I of a specular light intensity, upon measurement of the object S to be measured by the master machine (reference machine), that is, emission of the illumination light of spectral irradiance L(λ). Next, the gloss evaluation apparatus 100 obtains, using formula (2), an index value I' of specular light intensity, upon measurement of the object S to be measured by the gloss evaluation apparatus (relevant machine, own machine) 100, that is, emission of illumination light of spectral irradiance L'(λ).

Then, the gloss evaluation apparatus 100 calculates a coefficient K, based on a ratio between the index value I and the index value I', that is, using the following formula (3), corrects a specular light intensity a as output of the specular light reception unit 30, using formula (4), and obtains a specular light intensity P upon measurement by the master machine. The gloss evaluation value is calculated based on the specular light intensity P. For example, the specular light intensity P is standardized with an output value of a calibration plate (reference sample) to calculate the gloss evaluation value.

$$I = c \int L(\lambda) S(\lambda) d\lambda + b \int L(\lambda) R(\lambda) S(\lambda) d\lambda \quad (1)$$

$$I' = c \int L'(\lambda) S(\lambda) d\lambda + b \int L'(\lambda) R(\lambda) S(\lambda) d\lambda \quad (2)$$

$$K = I/I' \quad (3)$$

$$P = K \times a \quad (4)$$

Wherein, L(λ) is the spectral irradiance of the gloss measuring light source 11 of the first illumination unit 10 of the master machine, and L'(λ) is the spectral irradiance of the gloss measuring light source 11 of the first illumination unit 10 of the relevant gloss evaluation apparatus 100. S(λ) is the spectral sensitivity of the gloss detection device 32 of the specular light reception unit 30. The spectral irradiance L(λ) and the spectral sensitivity S(λ) are previously measured, and stored in the storage unit 53 upon shipment of the gloss evaluation apparatus 100. Note that the spectral sensitivities of the gloss detection device 32 of the master machine and the gloss detection device 32 of the gloss evaluation apparatus 100 are substantially equal to each other. Moreover, the spectral irradiance L'(λ) is obtained by measuring a white plate as the object S to be measured, using the diffuse reflection light receiving unit 20. Note that, the spectral irradiance L'(λ) may be measured directly from the light source, using the diffuse reflection light receiving unit 20.

In formula (4), a is a light intensity obtained by measuring the specular light from the object S to be measured by the gloss detection device 32, upon emission of the illumination light from the first illumination unit 10, as illustrated in FIG. 2.

In formulas (1) and (2), b is the light intensity obtained by measuring diffuse reflection light from the object S to be measured by the spectrum detection unit 22, upon emission of the illumination light from the first illumination unit 10, as illustrated in FIG. 2, and calculating a sum of outputs from the spectrum detection unit 22. In the embodiment, the sum of outputs from the spectrum detection unit 22 allows calculation of the light intensity b, but the light intensity may be measured by providing a photodiode, separating from the spectrum detection unit 22. Moreover, for the light intensity b, output of a wavelength may be used as a representative value.

In formulas (1) and (2), c is a Fresnel reflection intensity in specular components from a surface to be measured of the object S, upon emission of the illumination light from the first illumination unit 10, as illustrated in FIG. 2.

Figure 10:
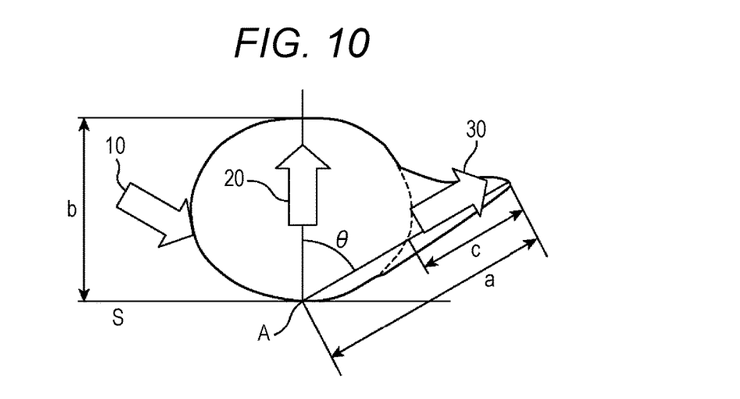
FIG. 10 is a diagram illustrating an intensity distribution of reflection light reflected on a surface to be measured of an object to be measured.

FIG. 10 is a diagram in which an intensity distribution of reflected light reflected from the surface to be measured upon emission of light to the surface to be measured of the object S to be measured by the first illumination unit 10 is represented according to magnitude of distance from the intersection point A. A white arrow 10 represents an illumination direction of the illumination light from the first illumination unit 10 of FIG. 2 (optical axis L1), a white arrow 20 represents a dispersion/reflection direction thereof (optical axis L2), and a white arrow 30 represents the specular direction thereof (optical axis L3).

In the intensity distribution illustrated in FIG. 10, a projecting portion represents the specular light (specular light component a), and the other portion represents diffuse light (specular light component b). Thus, the Fresnel reflection intensity c can be calculated using the following formula.

$$c = a - b \times d$$

Note that d is an intensity ratio (known coefficient) between angular intensity based on specular reflection measurement and angular intensity based on diffuse reflection measurement in cos characteristic, in which when a reflection angle θ is 60 degrees, d=cos 60 degrees=0.5.

R(λ) is the spectral intensity (spectral reflectance) obtained by measuring the diffuse reflection light from the object S to be measured by the spectrum detection unit 22, upon emission of illumination light from the second illumination unit 40, as illustrated in FIG. 3.

The spectral irradiances L'(λ) of the gloss measuring light sources 11 have individual differences, even if the light sources have an identical product number. For example, when a white LED is used as a light source, white color is made by mixing blue excitation light and yellow fluorescent light, and thus, blue color may be shifted in a wavelength direction. Moreover, temporal change or temperature or the like in a use environment may cause the individual difference.

The spectral irradiance L'(λ) is measured for each measurement, and the gloss measuring light source 11 of the first illumination unit 10 can be corrected thereby in output variation or temporal change. Note that, the spectral irradiance L'(λ) does not need to be corrected at each time of measurement, and may be corrected at suitable time. In this configuration, the spectral irradiance L'(λ) is also stored in the storage unit 53.

Since the specular light reception unit 30 measures the specular light passing through the filter 33, variation in spectral transmittance F(λ) of the filter 33 causes variation in specular light intensity a, but correction as described above can reduce such variation.

TABLE 1

| NUMBER | PARAMETER CONTENT | PARAMETER NAME | OBJECTIVE MACHINE | LIGHT SOURCE | OBJECT TO BE ILLUMINATED | MEASUREMENT LIGHT | DETECTION DEVICE |
| --- | --- | --- | --- | --- | --- | --- | --- |
| 1 | SPECTRAL IRRADIANCE OF GLOSS MEASURING LIGHT SOURCE 11 | $L(\lambda)$ | MASTER MACHINE | FOR GLOSS MEASUREMENT | REFERENCE PLATE NO OBJECT TO BE ILLUMINATED | DIFFUSE REFLECTION LIGHT DIRECT LIGHT SOURCE | FOR COLOR |
| 2 | SPECTRAL IRRADIANCE OF GLOSS MEASURING LIGHT SOURCE 11 | $L'(\lambda)$ | MACHINE TO BE CORRECTED | FOR GLOSS MEASUREMENT | REFERENCE PLATE NO OBJECT TO BE ILLUMINATED | DIFFUSE REFLECTION LIGHT DIRECT LIGHT SOURCE | FOR COLOR |
| 3 | SPECTRAL SENSITIVITY OF DETECTION DEVICE | $S(\lambda)$ | MASTER MACHINE, MACHINE TO BE CORRECTED (ASSUMING THAT THERE IS NO DIFFERENCE) | — | — | — | FOR GLOSS |
| 4 | SPECTRAL REFLECTION INTENSITY OF SAMPLE | R sample $(\lambda)$ | MACHINE TO BE CORRECTED | FOR COLOR MEASUREMENT | SAMPLE | DIFFUSE REFLECTION LIGHT | FOR COLOR |
| 5 | REFLECTION INTENSITY OF SAMPLE | a | MACHINE TO BE CORRECTED | FOR GLOSS MEASUREMENT | SAMPLE | SPECULAR LIGHT | FOR GLOSS |
| 6 | REFLECTION INTENSITY OF SAMPLE | b | MACHINE TO BE CORRECTED | FOR GLOSS MEASUREMENT | SAMPLE | DIFFUSE REFLECTION LIGHT | FOR COLOR |

Table 1 shows a parameter table of parameters used for the formulas (1) and (2). This parameter table includes "number" fields, "parameter content" fields, "parameter name" fields, "objective machine" fields, "light source" fields, "object to be illuminated" fields, "measurement light" fields, and "detection device" fields.

In the "number" field, parameter numbers "1" to "6" indicating the parameters are set. That is, six parameters are registered in this parameter table.

For the parameters having parameter numbers "1" to "6", in the "parameter content" fields corresponding to numbers registered in the "number" fields the contents of the parameters are set, and in the "parameter name" fields, the names of the parameters used for formulas (1) and (2) are set. In an "objective machine" field, an apparatus (master machine/machine to be corrected) for measuring a parameter having a corresponding number is set, in a "light source" field, a light source (for gloss measurement/for color measurement) for emitting light for measurement of the parameter having the corresponding number is set, and in an "object to be illuminated" field, an object (reference plate/no object to be illuminated/sample) to which light is emitted for measurement of the parameter having the corresponding number is set. In a "measurement light" field, light (diffuse reflection light/direct light source/specular light) to be measured for measurement of the parameter having the corresponding number is set, and in a "detection device" field, a device (for color/for gloss) for measuring light registered in the "measurement light" field is set.

In the "objective machine" fields, "master machine" represents the master machine as the reference machine, and "machine to be corrected" represents the gloss evaluation apparatus 100 being so-called mass-produced machine.

In the "light source" fields, "for gloss measurement" represents the specular light reception unit 30, and "for color measurement" represents the diffuse reflection light receiving unit 20.

In the "object to be illuminated" fields, "reference plate" represents a white reference plate, "no object to be illuminated" represents that there is not an object to be illuminated, and "sample" represents the object S to be measured.

In the "measurement light" fields, "diffuse reflection light" represents the diffuse reflection light from the white reference plate or the object S to be measured, "direct light source" represents the illumination light directly from the light source, and "specular light" represents the specular light from the white reference plate or the object S to be measured.

In the "detection device" fields, "for color" represents the diffuse reflection light receiving unit 20, and "for gloss" represents the specular light reception unit 30.

For example, for a parameter having the parameter number "1", "spectral irradiance of gloss measuring light source 11" is set in the "parameter content" field, "$L(\lambda)$" is set in the "parameter name" field, "master machine" is set in the "objective machine" field, "for gloss measurement" is set in the "light source" field, "reference plate" and "no object to be illuminated" are set in the "object to be illuminated" field, "diffuse reflection light" and "direct light source" are set in the "measurement light" field, and "for color" is set in the "detection device" field.

The above description shows that the parameter having the parameter number "1" is a parameter "$L(\lambda)$" used for formulas (1) and (2), the content of the parameter is "spectral irradiance of gloss measuring light source 11", the parameter is measured by the "master machine", the illumination light from the light source "for gloss measurement"

(second illumination unit 40) is emitted to the "reference plate", and "diffuse reflection light" reflected from the reference plate is obtained by being measured by the detection device "for color" (diffuse reflection light receiving unit 20). Moreover, the above description shows that illumination light from the light source "for gloss measurement" (second illumination unit 40) is obtained by being directly measured by the detection device "for color" (diffuse reflection light receiving unit 20).

<Operation>

Figure 11:
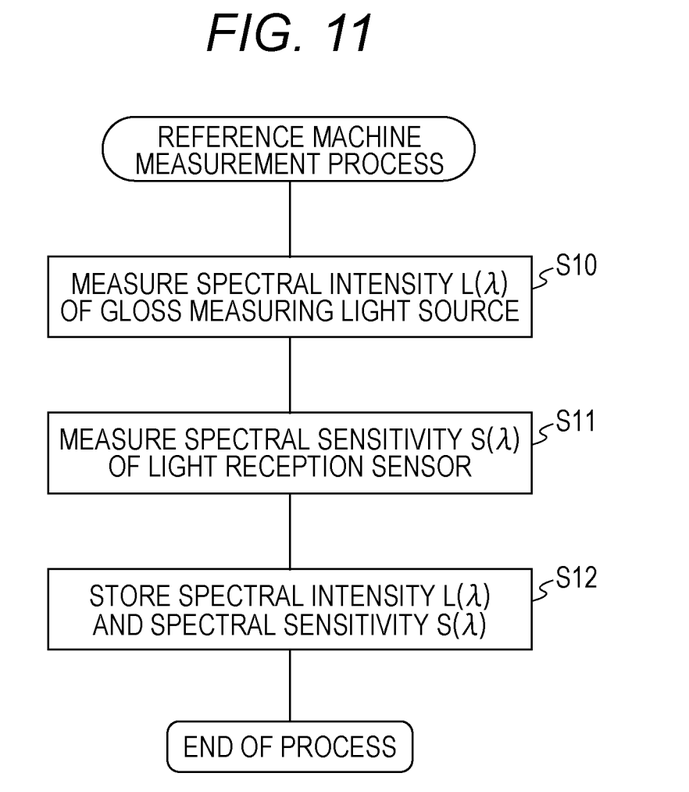
FIG. 11 is a flowchart of a reference machine measurement process.
Figure 12:
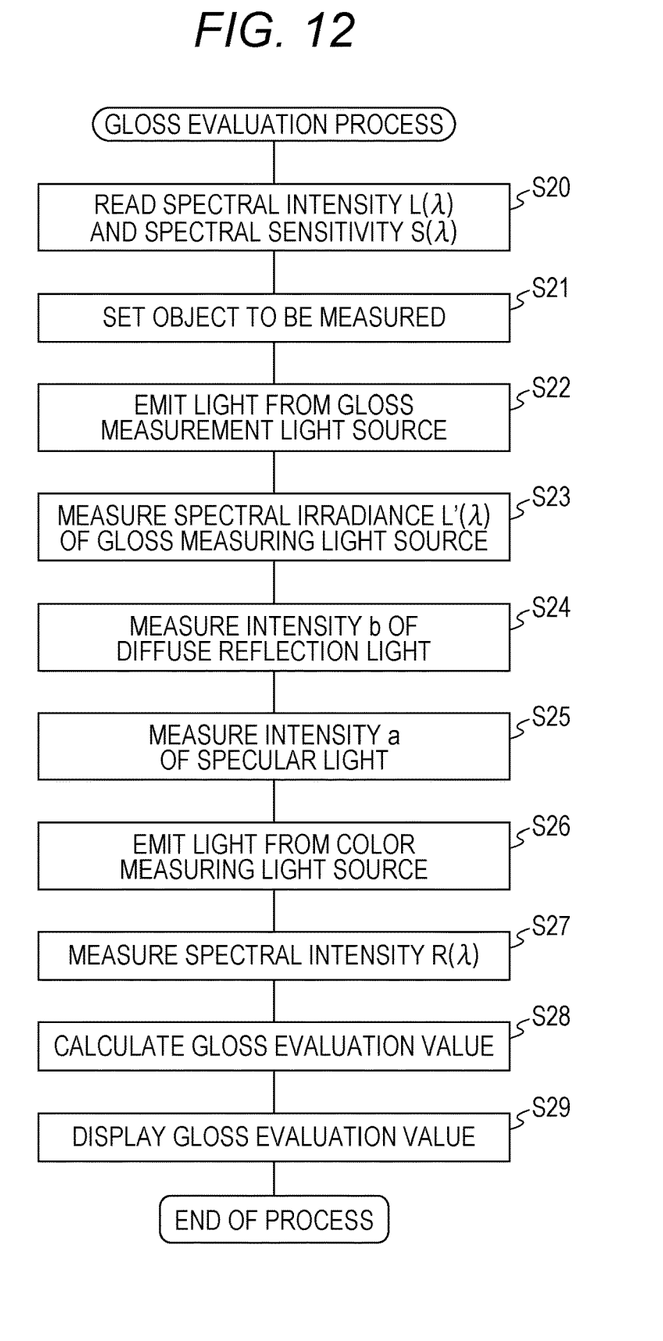
FIG. 12 is a flowchart of a gloss evaluation process.

Next, operation of the present embodiment will be described using FIGS. 11 and 12. FIG. 11 is a flowchart of a reference machine measurement process of the master machine, and FIG. 12 is a flowchart of a gloss evaluation process performed by the gloss evaluation apparatus 100.

First, the reference machine measurement process will be described using FIG. 11. The reference machine measurement process is performed in the master machine as a reference of the gloss evaluation value.

First, in the master machine, the spectral irradiance $L(\lambda)$ of the gloss measuring light source 11 of the first illumination unit 10 is measured (step S10). A measurement method may employ a measurement method in which the white reference plate is set as the object S to be measured, and the diffuse reflection light receiving unit 20 is used, or a method of measuring the illumination light from the gloss measuring light source 11.

Next, the spectral sensitivity $S(\lambda)$ of the specular light reception unit 30 is measured (step S11).

The measured spectral irradiance $L(\lambda)$ and spectral sensitivity $S(\lambda)$ are stored in the storage unit 53 (step S12). The stored spectral irradiance $L(\lambda)$ and spectral sensitivity $S(\lambda)$ are stored in the storage unit 53 of each gloss evaluation apparatus 100 before shipment.

Next, the gloss evaluation process in the gloss evaluation apparatus 100 will be described using FIG. 12.

Before a measurer uses the gloss evaluation apparatus 100 to start the gloss evaluation process, for example, upon shipment, the spectral irradiance $L(\lambda)$ and the spectral sensitivity $S(\lambda)$ in the master machine is stored in the storage unit 53.

The measurer uses the input unit 54 to input a command or the like for preparing the gloss evaluation process.

The calculation control unit 50 detecting, through the input unit 54, input of the command for preparing the gloss evaluation process reads the spectral irradiance $L(\lambda)$ and the spectral sensitivity $S(\lambda)$ from the storage unit 53, and stores them in a working memory (step S20). The calculation control unit 50 turns on the first illumination unit 10, the diffuse reflection light receiving unit 20, the specular light reception unit 30, and the second illumination unit 40, and instructs preparation required for measurement, and the functional units make preparations required for the measurement, such as initialization.

Next, the measurer sets the object S to be measured to a predetermined position, and inputs a command for starting the gloss measurement (step S21). The calculation control unit 50 detecting input of the command for starting the gloss measurement instructs the control unit 51 to start light emission from the gloss measuring light source 11.

The control unit 51 receiving the instruction drives the gloss measuring light emission circuit 12 to start the light emission from the gloss measuring light source 11 (step S22).

Next, the spectral intensity (spectral irradiance $L'(\lambda)$) from the spectrum detection unit 22 is input to the calculation control unit 50 (step S23), and stored in the working memory, and then, the outputs from the spectrum detection unit 22 are summed to calculate the light intensity b (step S24), and stored in the working memory.

Then, the specular light intensity a from the gloss detection device 32 is input to the calculation control unit 50 (step S25), and stored in the working memory.

The calculation control unit 50 stops the light emission from the gloss measuring light source 11, and instructs the control unit 51 to start light emission from the color measuring light emission circuit 42.

The control unit 51 receiving the instruction drives the gloss measuring light emission circuit 12 to stop the light emission from the gloss measuring light source 11, and then drives the color measuring light emission circuit 42 to start light emission from the color measuring light source 41 (step S26).

Next, the spectral intensity (spectral reflectance $R(\lambda)$) from the spectrum detection unit 22 is input to the calculation control unit 50 (step S27), and stored in the working memory.

Then, the calculation control unit 50 makes a request to the calculation unit 52 for calculation of the gloss evaluation value.

As described in <Process of finding gloss evaluation value>, the calculation unit 52 receiving the request uses formulas (1) to (4) to calculate the specular light intensity P, and calculates the gloss evaluation value based on the specular light intensity P (step S28).

The calculation unit 52 having calculated the gloss evaluation value displays the calculated gloss evaluation value on the input unit 54 (step S29).

The measurer sets a next object S to be measured, and inputs a measurement instruction to the input unit 54. The calculation control unit 50 receiving the measurement instruction starts processing of step S22 and subsequent steps.

As described above, even if the gloss measuring light source 11 varies in spectral irradiance $L(\lambda)$ or the filter 33 varies in spectral transmittance $F(\lambda)$, variation in evaluation value (measurement value) caused by a difference between machines can be reduced.

Techniques are disclosed according to various aspects in the present description as described above, but a main technique thereof will be summarized below.

According to an aspect, a gloss measurement method is a gloss evaluation method for obtaining an evaluation value about gloss of an object to be measured based on specular light and diffuse reflection light obtained from the object to be measured, the gloss evaluation method including obtaining an intensity P of specular light from an intensity a of specular light, based on an intensity b of dispersed reflected light, and a spectral reflectance $R(\lambda)$ of diffuse reflection light, the intensity P of specular light being obtained by illuminating an object to be measured with illumination light of spectral irradiance $L(\lambda)$, the intensity a of specular light being obtained by illuminating the object to be measured with first illumination light of spectral irradiance $L'(\lambda)$ from a first light source, the intensity b of dispersed reflected light being obtained by illuminating the object to be measured with the first illumination light, the spectral reflectance $R(\lambda)$ of diffuse reflection light being obtained by illuminating the object to be measured with predetermined second illumination light from a second light source, the second illumination light being emitted from an illuminating angle different from that of the first light source.

According to another aspect, a gloss evaluation apparatus includes a first light source emitting light of spectral irradiance L'(λ) to an object to be measured, a second light source emitting light to the object to be measured from an illuminating angle different from that of the first light source, a first detection unit having a spectral sensitivity S(λ) for detecting an intensity a of specular light from the first light source obtained from the object to be measured, a second detection unit detecting a spectral reflectance R(λ) of diffuse reflection light from the second light source obtained from the object to be measured, a third detection unit detecting an intensity b of diffuse reflection light from the first light source obtained from the object to be measured, and a calculation unit calculating an intensity P of specular light obtained upon emission of light of spectral irradiance L(λ) from the first light source, from the intensity a of the specular light, based on the spectral reflectance R(λ) and the intensity b of diffuse reflection light.

According to such a gloss measurement method and gloss evaluation apparatus, an intensity P of specular light is obtained from an intensity a of specular light, based on an intensity b of dispersed reflected light, and a spectral reflectance R(λ) of diffuse reflection light, the intensity P of specular light is obtained by emitting light of spectral irradiance L(λ) from a first light source, the intensity a of specular light is obtained by illuminating the object to be measured with first illumination light of spectral irradiance L'(λ) from a first light source, the intensity b of dispersed reflected light is obtained by illuminating the object to be measured with the first illumination light, the spectral reflectance R(λ) of diffuse reflection light is obtained by illuminating the object to be measured with second illumination light from a second light source, the second illumination light being emitted from an illuminating angle different from that of the first light source. Thus, even if spectral irradiance L'(λ) varies between apparatuses, the gloss measurement method and the gloss evaluation apparatus allow calculation of the intensity P of specular light within a certain spectral irradiance L(λ). That is, even if the spectral irradiance L'(λ) varies between the first light sources due to a difference between machines, variation caused by temporal change, or temperature or the like in a use environment, the intensity of specular light with reduced variation can be calculated. The gloss evaluation value is calculated based on the specular light intensity P, and thus, the gloss evaluation value can be calculated without variation caused by a difference between machines.

According to another aspect, in the above gloss measurement method, the intensity P of specular light is preferably obtained by multiplying the intensity a of specular light and a coefficient K being a ratio between an index value I of specular light and an index value I' of specular light. The index value I of specular light is obtained by illuminating the object to be measured with illumination light of spectral irradiance L(λ), calculated by formula (1), and the index value I' of specular light is obtained by illuminating the object to be measured with first illumination light of spectral irradiance L'(λ), calculated by formula (2).

In such a gloss measurement method, the coefficient K is obtained from the ratio between the index value I in emission of light of spectral irradiance L(λ), and the index value I' in emission of light of spectral irradiance L(λ), and thus, even if spectral irradiance L'(λ) varies between light sources, the intensity P of specular light can be calculated within a certain spectral irradiance L(λ).

According to another aspect, in the above gloss measurement methods, the intensity a of specular light is preferably measured by illuminating the object to be measured with first illumination light of spectral irradiance L'(λ) from a first light source, and receiving specular light from the object to be measured caused by the first illumination light, by a light reception sensor of spectral sensitivity S(λ) through a filter of spectral transmittance F(λ).

In such gloss measurement methods, even if the filter has a difference between machines in spectral transmittance F(λ) between the gloss evaluation apparatuses, the intensity P of specular light can be calculated within a certain spectral irradiance L(λ).

According to another aspect, in the above gloss measurement methods, spectral irradiance L'(λ) is preferably measured at each time of obtaining a gloss evaluation value of the object to be measured.

In such gloss measurement methods, the spectral irradiance L'(λ) is updated at each time of measurement, and thus, the intensity P of specular light can be calculated with reduced influence of temporal change.

According to another aspect, in the above gloss measurement methods, spectral irradiance L(λ) preferably is a spectral irradiance of illumination light emitted from a first light source of a reference machine.

Moreover, according to another aspect, in the above gloss measurement methods, the evaluation value of the object to be measured is preferably obtained by standardizing the intensity P of specular light using an evaluation value of a normal object to be measured.

With such gloss measurement methods, even if any apparatus is used to calculate the gloss evaluation value of the object to be measured, the evaluation value can be calculated reducing a difference with the gloss evaluation value measured by the reference machine.

This application is based on Japanese Patent Application No. 2013-235967 filed on Nov. 14, 2013, and the contents thereof are incorporated in the present application.

The present invention has been adequately and sufficiently explained hereinabove on the basis of embodiments thereof with reference to the appended drawings in order to describe the present invention, but it should be recognized that the embodiments could be easily changed and/or modified by a person skilled in the art. Accordingly, changes or modifications implemented by a person skilled in the art should be construed to be included in the scope of rights delineated in the claims, provided that the changes or modifications do not depart from the scope of rights delineated in the claims.

INDUSTRIAL APPLICABILITY

According to the present invention, the gloss evaluation method and the gloss evaluation apparatus can be provided.

The invention claimed is:

1. A gloss evaluation method for obtaining a gloss evaluation value of an object to be measured based on specular light and diffuse reflection light obtained from the object to be measured, the gloss evaluation method comprising:

obtaining an intensity P of specular light from an intensity a of specular light, based on an intensity b of dispersed reflected light and a spectral reflectance R(λ) of diffuse reflection light, the intensity P of specular light being obtained by making reference to a previously-stored spectral irradiance L(λ) that was previously measured by a reference machine illuminating the object to be measured with illumination light of spectral irradiance L(λ), the intensity a of specular light being obtained by illuminating the object to be measured with first illumination light of spectral irradiance L'(λ) from a first light source, the intensity b of dispersed reflected light being obtained by illuminating the object to be measured with the first illumination light, the spectral reflectance R(λ) of diffuse reflection light being obtained by illuminating the object to be measured with predetermined second illumination light from a second light source, the second illumination light being emitted from an illuminating angle different from that of the first light source; and calculating the gloss evaluation value based on the obtained intensity P of specular light.

2. The gloss evaluation method according to claim 1, wherein the intensity P of specular light is obtained by multiplying the intensity a of specular light and a coefficient K being a ratio between an index value I of specular light and an index value I' of specular light, the index value I of specular light being obtained by the reference machine previously illuminating the object to be measured with the illumination light of spectral irradiance L(λ), calculated by formula (1), the index value I' of specular light being obtained by illuminating the object to be measured with first illumination light of spectral irradiance L'(λ), calculated by formula (2), $$I=c\int L(\lambda)S(\lambda)d\lambda+b\int L(\lambda)R(\lambda)S(\lambda)d\lambda \quad (1)$$

$$I'=c\int L'(\lambda)S(\lambda)d\lambda+b\int L'(\lambda)R(\lambda)S(\lambda)d\lambda \quad (2)$$

I: an index value I of specular light obtained by the reference machine previously illuminating the object to be measured with the illumination light of spectral irradiance L(λ)

I': an index value I' of specular light obtained by illuminating the object to be measured with the first illumination light of spectral irradiance L'(λ)

S(λ): a spectral sensitivity, stored in a memory in advance based on a previous measurement by the reference machine of a light reception sensor for measuring an intensity a by receiving specular light obtained by the reference machine illuminating the object to be measured with the light of spectral irradiance L(λ)

c: a Fresnel reflection intensity in specular light obtained by illuminating the object to be measured with illumination light of spectral irradiance L'(λ).

3. The gloss evaluation method according to claim 2, wherein the intensity a of specular light is measured by illuminating the object to be measured with first illumination light of spectral irradiance L'(λ) from the first light source, and receiving specular light from the object to be measured caused by the first illumination light, by a light reception sensor of spectral sensitivity S(λ) through a filter of spectral transmittance F(λ).

4. The gloss evaluation method according to claim 1, wherein the intensity a of specular light is measured by illuminating the object to be measured with the first illumination light of spectral irradiance L'(λ) from the first light source, and receiving specular light from the object to be measured caused by the first illumination light, by a light reception sensor of spectral sensitivity S(λ) through a filter of spectral transmittance F(λ).

5. The gloss evaluation method according to claim 4, wherein spectral irradiance L'(λ) is measured at each time of obtaining a gloss evaluation value of the object to be measured.

6. The gloss evaluation method according to claim 4, wherein spectral irradiance L(λ) is a spectral irradiance of illumination light emitted from a first light source of the reference machine.

7. The gloss evaluation method according to claim 4, wherein the evaluation value of the object to be measured is obtained by standardizing the intensity P of specular light using an evaluation value of a reference object to be measured.

8. The gloss evaluation method according to claim 1, wherein spectral irradiance L'(λ) is measured at each time of obtaining a gloss evaluation value of the object to be measured.

9. The gloss evaluation method according to claim 8, wherein spectral irradiance L(λ) is a spectral irradiance of illumination light emitted from a first light source of the reference machine.

10. The gloss evaluation method according to claim 8, wherein the evaluation value of the object to be measured is obtained by standardizing the intensity P of specular light using an evaluation value of a reference object to be measured.

11. The gloss evaluation method according to claim 1, wherein spectral irradiance L(λ) is a spectral irradiance of illumination light emitted from a first light source of the reference machine.

12. The gloss evaluation method according to claim 11, wherein the evaluation value of the object to be measured is obtained by standardizing the intensity P of specular light using an evaluation value of a reference object to be measured.

13. The gloss evaluation method according to claim 1, wherein the evaluation value of the object to be measured is obtained by standardizing the intensity P of specular light using an evaluation value of a reference object to be measured.

14. The gloss evaluation method according to claim 2, wherein spectral irradiance L'(λ) is measured at each time of obtaining a gloss evaluation value of the object to be measured.

15. The gloss evaluation method according to claim 2, wherein spectral irradiance L(λ) is a spectral irradiance of illumination light emitted from a first light source of the reference machine.

16. The gloss evaluation method according to claim 2, wherein the evaluation value of the object to be measured is obtained by standardizing the intensity P of specular light using an evaluation value of a reference object to be measured.

17. A gloss evaluation apparatus comprising:

a first light source emitting light of spectral irradiance L'(λ) to an object to be measured;

a second light source emitting light to the object to be measured from an illuminating angle different from that of the first light source;

a first detector having a spectral sensitivity S(λ) for detecting an intensity a of specular light from the first light source obtained from the object to be measured;

a second detector for detecting a spectral reflectance R(λ) of diffuse reflection light from the second light source obtained from the object to be measured;

a third detector for detecting an intensity b of diffuse reflection light from the first light source obtained from the object to be measured;

a memory storing a spectral irradiance $L(\lambda)$ from a first light source of a reference machine and measured by the reference machine illuminating the object to be measured with illumination light of the spectral irradiance $L(\lambda)$;
and
a calculator for calculating an intensity P of specular light obtained upon emission of light of the stored spectral irradiance $L(\lambda)$ from the first light source of the reference machine, from the intensity a of the specular light, based on the spectral reflectance $R(\lambda)$ and the intensity b of diffuse reflection light, the calculator calculating the gloss evaluation based on the calculated intensity P of specular light.

\* \* \* \* \*